United States Patent
Turner et al.

(12) 
(10) Patent No.: US 6,280,426 B1
(45) Date of Patent: *Aug. 28, 2001

(54) ABSORBENT ARTICLE WITH A FLAP AND BIASING SPACER

(75) Inventors: Laura Jean Turner, Appleton; Barbara Oakley Sauer, Fremont, both of WI (US)

(73) Assignee: Kimberly-Clark Worldwide, Inc., DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/253,471

(22) Filed: Feb. 19, 1999

(51) Int. Cl.$^7$ .................................................... A61F 13/15

(52) U.S. Cl. ........................... 604/385.01; 604/385.101

(58) Field of Search ...................... 604/378, 385.01, 604/385.201, 385.19, 385.101, 385.23

(56) References Cited

U.S. PATENT DOCUMENTS

| | | | |
|---|---|---|---|
| 4,704,116 | 11/1987 | Enloe | 604/385 A |
| 4,728,326 | 3/1988 | Gilles . | |
| 4,753,646 | 6/1988 | Enloe | 604/385 R |
| 4,778,459 | 10/1988 | Fuisz | 604/378 |
| 4,798,603 | 1/1989 | Meyer et al. | 604/378 |
| 5,026,364 | 6/1991 | Robertson | 604/385.1 |
| 5,069,672 | 12/1991 | Wippler et al. . | |
| 5,171,236 | 12/1992 | Dreier et al. | 604/369 |
| 5,176,668 | 1/1993 | Bernardin | 604/368 |
| 5,176,672 | 1/1993 | Bruemmer et al. | 604/385.1 |

(List continued on next page.)

FOREIGN PATENT DOCUMENTS

| | | |
|---|---|---|
| 0 355 740 A3 | 2/1990 | (EP) . |
| 0 820 746 A1 | 1/1998 | (EP) . |
| 2284537 A | 6/1995 | (GB) . |
| WO 95/00089 A1 | 1/1995 | (WO) . |
| WO 96/07381 A2 | 3/1996 | (WO) . |
| WO 96/07382 A2 | 3/1996 | (WO) . |
| WO 96/09026 A2 | 3/1996 | (WO) . |

(List continued on next page.)

*Primary Examiner*—Richard K. Seidel
*Assistant Examiner*—Michael M. Thompson
(74) *Attorney, Agent, or Firm*—Michael J. Bendel

(57) ABSTRACT

An absorbent article having a flap and a spacer wherein the flap is positioned in the rear waist portion of the article and forms a pocket. The spacer is positioned proximate the pocket opening and biases the pocket into an open position. The flap may be a laterally extending liquid impermeable flap which is fixedly secured to the article along a seam. The seam, which may be substantially U-shaped, extends between first and second terminal ends. The flap has a free edge which extends between the first and second terminal ends of the seam. The seam and free edge of the flap define the boundaries of a pocket which is formed between the flap and a topsheet of the absorbent article. The pocket has an opening extending between the first and second terminal ends of the seam. The spacer affixed to the article whereby it is disposed between the flap and the backsheet proximate, and optionally extending through, the pocket opening to bias the free edge of the flap away from the topsheet. Alternative spacer embodiments may be employed. A single spacer or two spacers positioned on opposite sides of the longitudinal axis of the article may be used to bias the pocket open. The use of a spacer which dynamically biases the flap away from the topsheet automatically adjusts the size of the pocket opening in response to relative movement between the wearer and the absorbent article. One or more hinged spacers may be employed to provide such a dynamic spacer.

17 Claims, 2 Drawing Sheets

U.S. PATENT DOCUMENTS

| | | |
|---|---|---|
| 5,188,626 | 2/1993 | Toyoda et al. . |
| 5,192,606 | 3/1993 | Proxmire et al. .................... 428/284 |
| 5,306,266 | 4/1994 | Freeland ............................ 604/385.1 |
| 5,330,459 | 7/1994 | Lavon et al. ...................... 604/385.1 |
| 5,397,318 | 3/1995 | Dreier ............................... 604/385.2 |
| 5,445,627 | 8/1995 | Mizutani et al. ................. 604/385.2 |
| 5,509,915 | 4/1996 | Hanson et al. ....................... 604/378 |
| 5,514,121 * | 5/1996 | Roe et al. ......................... 604/385.1 |
| 5,520,674 | 5/1996 | Lavon et al. ...................... 604/385.1 |
| 5,531,730 | 7/1996 | Dreier . |
| 5,558,660 * | 9/1996 | Dreir ............................... 604/385.2 |
| 5,558,661 * | 9/1996 | Roe et al. ......................... 604/385.2 |
| 5,582,604 | 12/1996 | Ahr et al. ......................... 604/385.1 |
| 5,601,543 | 2/1997 | Dreier et al. . |
| 5,618,281 | 4/1997 | Betrabet et al. ..................... 604/387 |
| 5,658,270 | 8/1997 | Lichstein ............................ 604/387 |
| 5,749,866 | 5/1998 | Roe et al. ......................... 604/385.2 |
| 5,814,037 | 9/1998 | Coates . |
| 5,833,677 | 11/1998 | Sauer ................................ 604/369 |
| 5,902,297 | 5/1999 | Sauer ............................... 604/385.1 |
| 5,938,652 | 8/1999 | Sauer ............................... 604/385.2 |
| 6,017,336 | 1/2000 | Sauer . |
| 6,022,338 | 2/2000 | Putzer . |

FOREIGN PATENT DOCUMENTS

| | | |
|---|---|---|
| WO 96/13238 A1 | 5/1996 | (WO) . |
| WO 96/20670 A1 | 7/1996 | (WO) . |
| WO 96/20674 A1 | 7/1996 | (WO) . |
| WO 96/34589 A2 | 11/1996 | (WO) . |
| WO 97/17926 A1 | 5/1997 | (WO) . |
| WO 97/22319 A1 | 6/1997 | (WO) . |
| WO 97/48357 A1 | 12/1997 | (WO) . |
| WO 97/49366 A1 | 12/1997 | (WO) . |

* cited by examiner

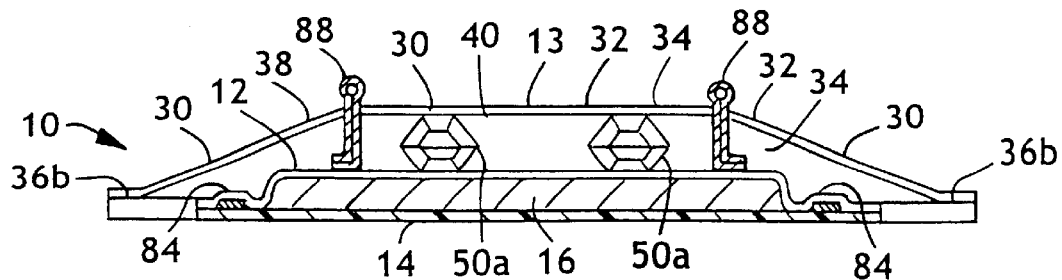
FIG. 3
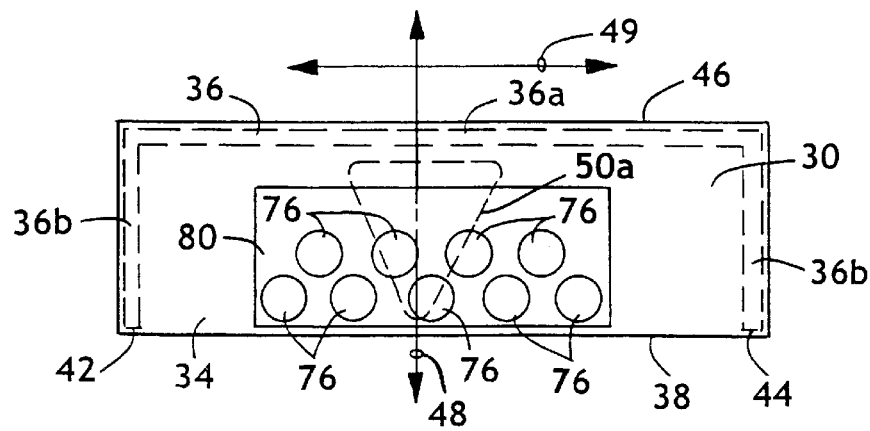
FIG. 4
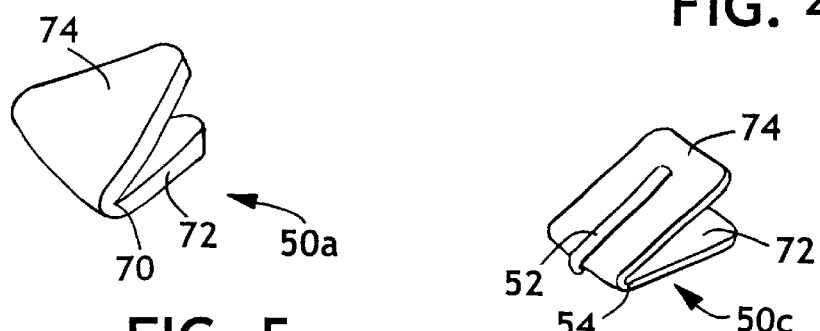
FIG. 5
FIG. 7
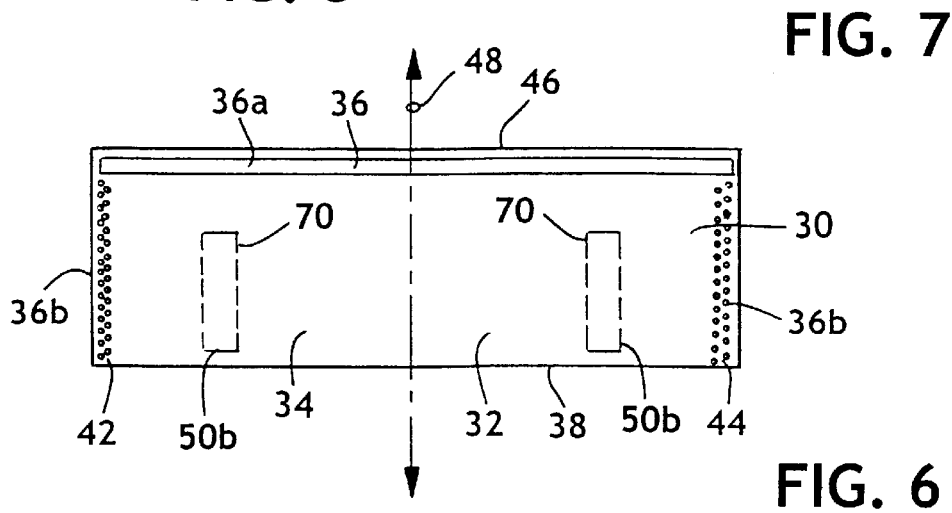
FIG. 6

ABSORBENT ARTICLE WITH A FLAP AND BIASING SPACER

BACKGROUND OF THE INVENTION

The present invention relates to absorbent articles and, more specifically, to absorbent articles such as disposable diapers, training pants and incontinence garments which are intended to receive and contain fecal insults.

Absorbent articles such as disposable diapers, training pants, incontinence garments and similar items are well known in the art. Such absorbent articles conventionally include an absorbent material for absorbing bodily exudates and include a front portion disposed adjacent the front pelvic or lower abdominal region of the wearer, a rear portion disposed adjacent the rear pelvic or lower abdominal region of the wearer and a crotch portion interconnecting the front and rear portions of the article and disposed between the legs of the wearer.

Many such conventional absorbent articles, and diapers in particular, are typically secured about the waist of the wearer using fasteners which are releasably engageable, i.e., refastenable. Such articles also often include elasticized, longitudinally extending barrier flaps which are positioned along the upper inner thighs of the wearer and inhibit the escape of exudates from between the absorbent article and legs of the wearer. Such articles are also known to include waist flaps in either or both the front and rear waist regions of the article to inhibit the escape of exudates from between the absorbent article and either the front or rear pelvic or lower abdominal region of the wearer. It is also known to provide absorbent articles with various forms of voids or pockets for receiving and containing bodily exudates.

SUMMARY OF THE INVENTION

The present inventors have recognized difficulties and problems inherent in the prior art and in response thereto have developed an improved absorbent article having a flap and a spacer assembly. The flap is positioned in the rear waist portion of the article and forms a pocket while the spacer assembly is positioned proximate the pocket opening.

In one aspect, the present invention concerns an absorbent article which has a bodyside surface which is positioned adjacent the crotch and rear waist regions of a wearer when the article is in use and wherein the bodyside surface of the article includes a laterally central, longitudinal axis, e.g., a longitudinal centerline. The article comprises, i.e., includes but is not limited to, a backsheet, a liquid permeable topsheet attached to the backsheet and an absorbent structure disposed between the backsheet and the topsheet. A laterally extending liquid impermeable flap is disposed in the rear waist portion of the article and is fixedly secured to the article along a seam. The seam, which may be substantially U-shaped, extends between first and second terminal ends. The flap has a free edge which extends between the first and second terminal ends of the seam. The seam and free edge of the flap define the boundaries of a pocket which is formed between the flap and the topsheet and which has an opening extending between the first and second terminal ends of the seam. The article further includes a spacer affixed to the article. The spacer is disposed between the flap and the backsheet and is positioned proximate the pocket opening. The spacer includes a first element in contact with the flap and a second element disposed between the first element and the backsheet. A biasing element forcibly separates the first and second elements of the spacer whereby the free edge of the flap is biased away from the topsheet.

Alternative embodiments of the present invention may also include a second spacer disposed between the flap and the backsheet. One of the spacers may be positioned in proximity to the first terminal end, while the second spacer may be positioned in proximity to the second terminal end. The pocket opening may extend substantially laterally whereby the two spacers are disposed on opposite lateral sides of the longitudinal axis. The laterally central portion of such a pocket opening would be disposed between the two spacers.

In some embodiments, the spacer of the present invention may be formed by folding a material to thereby create a resilient hinge at the fold line of the material. Other embodiments may employ two spacers disposed on opposite sides of the longitudinal axis whereby a laterally central portion of the free edge is disposed between the two spacers and biased away from the topsheet.

Still other spacers which can be used with the present invention may be formed with a resiliently compressible material or may extend through the pocket opening. Additional alternative embodiments of the present invention may include a flap which is formed with a liquid permeable material.

An advantage of the present invention is that the spacer maintains a separation between the flap and the topsheet at the pocket opening. This maintains the pocket opening in a position adapted for receiving fecal insults. Fecal materials which are contained within the pocket are thereby removed from contact with the wearer's skin while the article is being worn and reduces the opportunity for the fecal material to contact the skin or clothing of either the wearer or the caregiver during the removal of the article from the wearer.

Another advantage of the present invention is that the biasing element of the spacer dynamically biases the flap away from the topsheet at the pocket opening thereby enhancing the functionality of the flap for an active wearer. As a wearer moves, the absorbent article may shift relative to the wearer. This may cause the distance between the topsheet and the rear waist region of the wearer to vary in response to the wearer's movements. By providing a dynamically biasing spacer, the flap opening can be automatically adjusted in coordination with the wearer's movements and thereby inhibit the formation of a gap between the flap's free edge and the wearer through which bodily exudates might escape.

BRIEF DESCRIPTION OF THE DRAWINGS

The invention will be more fully understood and further advantages will become apparent when reference is made to the following detailed description of the invention and the accompanying drawings, in which:

FIG. 3 is a is a cross-sectional view taken along line 3—3 of FIG. 1;

FIG. 4 is a top view of an alternative flap and spacer;

FIG. 5 is a perspective view of a spacer;

FIG. 6 is a top view of an alternative flap and spacer; and

FIG. 7 is a perspective view of an alternative spacer.

Figure 1:
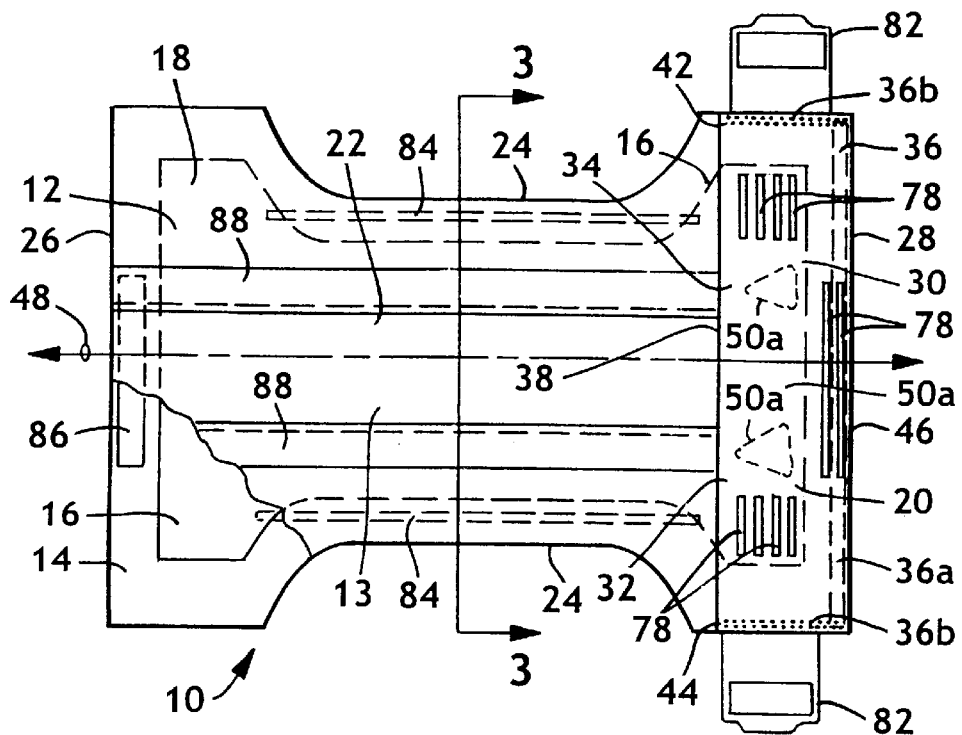
FIG. 1 is a partially cut-away top view of an absorbent article in accordance with the present invention.

Corresponding reference characters indicate corresponding parts throughout the several views. The disclosed embodiments are set forth to illustrate and exemplify the invention. The disclosed embodiments are not intended to be an exhaustive illustration of the invention or to be construed as limiting the scope of the invention to the precise forms disclosed.

DETAILED DESCRIPTION OF THE INVENTION

The following detailed description is made in the context of a disposable diaper which is adapted to be worn by infants about the lower torso. It is readily apparent, however, that the present invention is also applicable with other absorbent articles, such as incontinence garments, training pants, and other similar articles, which are used to absorb or contain bodily exudates.

Figure 2:
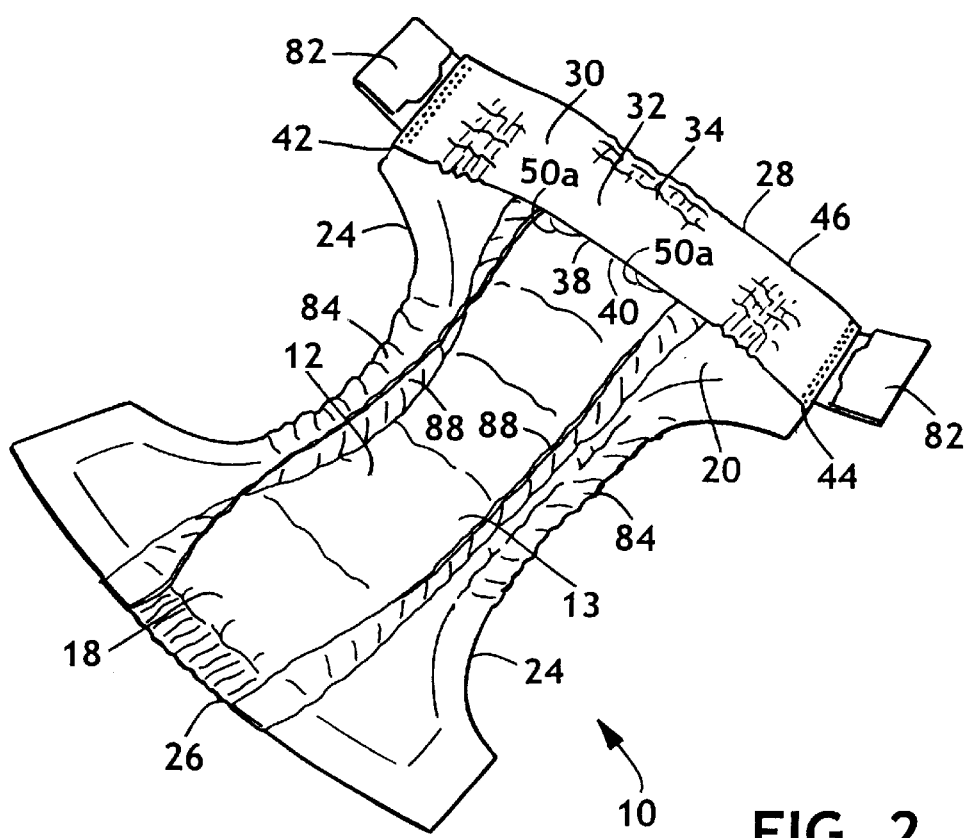
FIG. 2 is a perspective view of the absorbent article of FIG. 1.

With reference to FIGS. 1–3, an absorbent article in the form of a disposable diaper 10 is illustrated. The disposable diaper 10 has a chassis which includes a liquid permeable topsheet 12, a backsheet 14 and an absorbent structure 16 disposed between the topsheet 12 and the backsheet 14.

The disposable diaper 10 is adapted to be worn about the lower torso and to extend through the crotch of a wearer. The diaper 10 includes a front waist section 18, a rear waist section 20 and an intermediate section 22 which interconnects the front and rear waist sections. As used herein, reference to the front of an absorbent article refers to that portion of the absorbent article which is generally located at the front of the wearer when the article is in use while the rear of the article refers to that portion of the article which is generally located at the rear of the user when in use.

The lateral edges of the intermediate section 22 are defined by a pair of oppositely disposed side edges 24 while the edges of the front 18 and rear 20 waist sections are respectively defined by longitudinally opposed and laterally extending front waist end edge 26 and rear waist end edge 28.

The front 18 and rear 20 waist sections or regions include the general portions of the diaper 10 which are constructed to substantially and respectively extend over the wearer's front and rear abdominal regions during use. The intermediate section 22 includes the general portion of the diaper 10 which is constructed to extend through the wearer's crotch region between the legs. The opposed side edges 24 define leg openings and are typically contoured to closely fit the legs of the wearer. The opposed end edges 26, 28 define a waist opening and, in a top view such as FIG. 1, are typically straight but may also be curvilinear.

FIG. 1 is a top plan view of the diaper 10 in a flat, uncontracted state with the surface of the diaper which contacts the wearer, i.e., the bodyside or body facing surface 13, facing the viewer. As can be seen in FIG. 1, the disposable diaper 10 also includes a rear flap 30 which is located in the rear waist region 20 of the diaper 10.

Flap 30 includes two oppositely disposed major surfaces 32, 34. The first major surface 32 faces the body of the wearer during use of the article and forms a portion of the body facing surface 13 of the diaper 10 as shown in FIG. 1. Thus, the bodyfacing surface 13 of the diaper 10 is primarily formed by topsheet 12 and the first major surface 32 of the flap 30. The second major surface 34 of the flap 30 faces the topsheet 12 and is shown in FIG. 3. The space between the second major surface 34 and the topsheet 12 forms a pocket for containing fecal materials.

The flap 30 illustrated in FIG. 1 is attached to the diaper 10 along a seam 36 having a rear portion 36a and two oppositely disposed side portions 36b. As used herein, the term "seam" does not designate the method of construction used to join two parts together but is used instead to refer to the area or one or more points along which separate parts are joined together. The flap may be attached to the absorbent article by any of the numerous means known to those skilled in the art such as adhesive bonding, ultrasonic bonding, thermal bonding and the like or with a combination of different such means.

In the embodiment illustrated in FIG. 1, the seam 36 includes a rear portion 36a which extends in a lateral direction near the rear end edge 28 which adhesively joins the flap 30 to the topsheet 12. The rear portions 36a of the seams 36 illustrated in FIGS. 4 and 6 are also adhesive seams.

The seam 36 illustrated in FIG. 1 also includes two side portions 36b which are formed by a plurality of discrete ultrasonic welds. Similarly, the flap illustrated in FIG. 6 also includes a seam 36 having an adhesive rear portion 36a and two side portions 36b which are formed with ultrasonic welds. The seam 36 illustrated in FIG. 4 is an entirely adhesive seam. Alternative embodiments of the seam 36, such as a seam which is formed entirely with ultrasonic welds, may also be used with the present invention.

The illustrated seams 36 terminate at two terminal ends, i.e., a first terminal end 42 and a second terminal end 44. The seam 36 fixedly secures the flap 30 to the diaper 10. In other words, the flap 30 is secured along the seam in a permanent manner which does not allow relative movement between the article and the flap at the seam. The flap is not, however, directly attached to the article along an edge of the flap which extends between the terminal ends 42 and 44. This unattached portion of flap edge forms a free edge 38 extending between terminal ends 42 and 44.

Although all of the illustrated seams 36 have a generally rectilinear "U" shape, other configurations which define a pocket and an opening may be used with the present invention. In general, such pockets may be described as including a substantially continuous seam which terminates at two separate points wherein a line drawn between two such points, together with the seam, defines a closed figure having an area.

The free edge 38 of the flap 30 may move relative to the topsheet 12. When the free edge 38 is spaced from the topsheet 12, an opening 40 between the free edge 38 and the topsheet 12 is formed. This opening 40 provides access to the pocket which is formed between the flap 30 and the topsheet 12.

Free edge 38 is advantageously positioned on the diaper 10 such that it is located above the anus of the wearer when the diaper 10 is in use. It is also advantageous to position the free edge 38 of the flap on the diaper 10 so that it will be located above the gluteal groove of the wearer when the diaper 10 is in use. It is also generally advantageous to configure the opening 40 and pocket whereby the opening 40 is located at the longitudinally forward edge of the flap 30. Positioning the pocket opening above the gluteal groove of the wearer allows the pocket formed by the flap 30 and topsheet 12 to be well-positioned to receive and contain fecal materials expelled by the wearer, such as those materials which travel upwards along the gluteal groove. In small infants in particular, low viscosity fecal materials may be forced along the gluteal groove of the wearer. The free edge 38 is not limited to such positions, however, and may be positioned at a variety of locations on the bodyfacing surface 13 of the article.

Containing fecal materials in the pocket formed by the flap 30 limits the amount of contact between the fecal materials and the skin of the wearer while the article is being worn. Limiting the amount of contact with fecal materials can provide skin health benefits to the wearer. Containing fecal materials in the pocket formed by the flap 30 also reduces the chances of contact between the fecal materials and the skin and clothing of either the wearer or the caregiver during the removal process.

The illustrated free edge 38 of flap 30 extends in a substantially lateral direction and defines the longitudinally front edge of the flap 30. Alternative configurations of the flap 30, however, may include curvilinear or v-shaped front edges or other shapes which contour the free edge 38 of the flap to the body of the wearer.

The rear edge 46 of the flap 30 coincides with the rear end edge 28 of the absorbent article in the embodiment illustrated in FIGS. 1–3. The rear edge 46 of the flap 30, however, may be positioned in an alternative location such as along a line on the bodyside surface 13 spaced longitudinally forward of rear end edge 28. Those having ordinary skill in the art will also recognize that absorbent articles in accordance with the present invention may include flaps which are attached in further alternative configurations which form a rear pocket in addition to those which are explicitly disclosed herein to illustrate the present invention.

For the majority of individuals who wear absorbent garments and, in particular, for infants, the small or central portion of the wearer's back is generally concave, i.e., bowed inwards, or flat. As a result, a gap may easily form between the absorbent article and the wearer at this location. The absorbent articles of the present invention include flaps which are positioned in the rear waist region of the absorbent article whereby the pocket opening 40 formed by the flap's free edge 38 will be generally located in or near this area between the absorbent article and the small of the wearer's back when the article is placed on a wearer.

Spacers located between the flap 30 and the backsheet 14 are used to bias the flap's free edge 38 away from the topsheet and towards the skin of the wearer into an "open" position. In this manner the pocket opening 40 is maintained in an "open" position for receiving fecal materials. The spacers of the present invention may take a wide variety of forms and several spacer embodiments, 50a–c, are illustrated herein. Those having ordinary skill in the art will recognize that additional embodiments may also be employed in accordance with the invention described herein. Additional spacer embodiments are described in U.S. patent application Ser. No. 09/253,464, filed simultaneously herewith by Sauer et al., entitled "Absorbent Article Having a Flap and Spacer" and having the disclosure of which is incorporated herein by reference. The terms "spacer" and "spacer assembly" are used interchangeably herein and both terms may refer to an assemblage of either one or more parts.

When the pocket opening 40 is positioned in the area adjacent the small of the wearer's back, the pocket is well positioned for receiving bodily exudates such as low viscosity fecal materials which are forcibly transported along the gluteal groove of the wearer. U.S. patent application Ser. No. 08/575,926 (Faulks et al.) entitled "Absorbent Article Having A Rear Reservoir With Void Volume Capacity" having a filing date of Dec. 20, 1995 also discloses pockets positioned in the rear portion of a diaper and is incorporated herein by reference. Positioning the pocket opening 40 adjacent the small of the wearer's back may also facilitate the performance of the pocket by placing the pocket opening in an area where there is space available for the pocket opening 40 to be biased into an "open" position. The pocket opening 40 can also be positioned at other locations, such as in the front waist region of the diaper 10 where the pocket would be well positioned to inhibit the escape of urine.

The spacers of the present invention are affixed to the absorbent article in a position between the flap and the backsheet 14 whereby the free edge 38 of the flap 30 is biased away from the topsheet 12 to thereby form an opening 40. Advantageously, at least a portion of the spacer is disposed between the flap 30 and the topsheet 12. As exemplified by the embodiments illustrated herein, it can also be advantageous to locate the entirety of the spacer between the flap 30 and topsheet 12. The term "affix" is used herein to mean non-releasably attach. Thus, two items which are affixed together are intended to remain attached under normal use conditions.

The spacers of the present invention may be affixed to the diaper 10 in a number of different manners including the use of adhesives, ultrasonic welding, thermal welding and other attachment methods known to those skilled in the art. The spacer may be affixed to any portion of the diaper 10 which allows the spacer to bias the free edge 38 of the flap 30 away from the topsheet 12. Generally, it will be advantageous to directly attach the spacer to either the flap 30 or the topsheet 12 and position at least a portion of the spacer between the flap 30 and topsheet 12. In some embodiments, it may be most efficient to attach the spacer between the flap 30 and the topsheet 12 at the flap seam 36 and in the same manufacturing operation which attaches the flap 30 to the article.

The illustrated spacers 50a–c are affixed to the diaper 10 whereby at least a portion of the spacer is disposed between the flap 30 and the topsheet 12 and positioned in proximity to the pocket opening 40. By positioning at least a portion of the spacer in proximity to the pocket opening 40, the spacer will bias the flap 30 out of contact with the topsheet 12 at the pocket opening and thereby maintain the pocket in an "open" position. The configuration of the spacer, flap and topsheet will affect the extent to which the spacer separates the flap 30 from the topsheet 12 and, hence, how close the spacer must be to the pocket opening 40 to be sufficiently proximate to the opening 40 to bias the flap 30 and topsheet 12 into an "open" position. Generally, the spacer should be no more than about 5 to about 8 mm away from the free edge 38 of the flap 30.

Advantageously, the spacers are positioned to have a portion thereof which contacts the flap 30 immediately adjacent the free edge 38 or which extends through the pocket opening 40. By positioning a portion of the spacer immediately adjacent the free edge 38 of the flap 30 or by extending the spacer through the pocket opening 40, the free edge 38 of the flap is unlikely to "roll over" the front edge of the spacer and be inclined towards the topsheet. If the flap 30 is inclined towards the topsheet 12 as it extends to the free edge 38, the flap may act like a ramp and result in the undesirable movement of fecal materials between the flap 30 and the wearer rather than through the pocket opening 40 between the flap 30 and the topsheet 12.

Spacer 50a, best seen in FIG. 5, is a dynamic spacer which resiliently biases the flap 30 away from the topsheet 12 at the opening 40. As used herein, a "dynamic" spacer is a spacer which resiliently biases the flap 30 away from the topsheet 12 in such a manner as to cause the distance between the flap 30 and the topsheet 12 to vary in a substantially proportionate manner to variances in the distance between the topsheet 12 and the wearer at the pocket opening 40 due to the wearer's movements. By providing such a dynamically biasing spacer, the pocket opening 40 will automatically adjust in coordination with the wearer's movements to inhibit the formation and limit the size of any gap between the flap 30 and the wearer through which fecal materials might escape.

Such dynamic spacers may be formed by spring-like spacers, bellows-type spacers, or those including a hinge. As illustrated by spacer 50a, a hinged spacer may be formed by a folded material in which the fold line 70 forms the hinge. Scoring may be used in the formation of the fold line. The hinge 70 connects a first element 72 and a second element 74 wherein the first element 72 contacts the topsheet 12 and the second element 74 contacts the flap 30.

A biasing element is used to exert a separation force between the first and second elements 72, 74 and the spacer is positioned in proximity to the opening 40 whereby the first and second elements 72, 74 bias the flap 30 away from the topsheet 12 at the pocket opening 40. In the illustrated spacer 50a, the biasing element is inherent in the resilient hinge 70 formed by folding the spacer material. Folding the closed cell foam material used to form spacer 50a compresses the material near the fold line or hinge 70. Compression of the material at hinge 70 creates a force tending to separate the first and second elements 72, 74. Materials having a "memory" are also well-suited for forming such a resilient hinge.

The first and second elements 72, 74 of the illustrated spacer 50a each have a substantially triangular shape. As can be seen in FIG. 4, the spacer 50a may be positioned whereby the triangular shaped elements 72, 74 will be situated to conform with the upper end of the wearer's gluteal groove when the absorbent article is placed on the wearer. It may also be advantageous for either or both of the first and second elements 72, 74 to extend through the pocket opening 40. Alternatively, and as shown in FIGS. 1–3, two hinged spacers 50a can be placed on opposite sides of the longitudinal axis 48 thereby leaving the laterally central portion of the pocket opening 40 free of spacers.

As shown in FIG. 5, a closed cell foam material having a thickness of approximately 0.95 cm (3/8 inch) and a length of approximately 8.89 cm (3.5 inches) may be folded in half to form the illustrated spacers 50a. Spacers 50a have a width of approximately 2.54 cm (1 inch) at their folded hinge 70 and are tapered inwardly to a width of less than about 1.27 cm (0.5 inch) at the tips of the first and second elements 72, 74. The use of alternative materials might permit the spacer to have a thinner cross section and thereby permit a larger percentage of the pocket opening in the z-direction, i.e., the direction mutually perpendicular to both the lateral and longitudinal axes, to be unobstructed.

Alternative embodiments of the biasing element may be formed with spring-like mechanisms disposed between the first and second elements 72, 74; a resiliently compressible block of material disposed between the first and second elements 72, 74; or an elastic material attached to one or both of the first and second elements 72, 74 and/or the topsheet 12 or the flap 30.

For example, spacer 50c illustrated in FIG. 7 employs an elastic material 52 to provide the biasing element. Elastic material 52 is attached at its respective ends to first element 72 and second element 74 of the spacer 50c. The first and second elements 72, 74 are pivotally connected by a hinge 54 formed by scoring spacer 50c.

A coiled wire hinge, similar to that found in common safety pins, can also be used to form a biasing element. Such a coiled wire hinge could be completely or partially embedded within a plastic material to minimize the possibility of discomfort to the wearer.

Some embodiments of the present invention may include two or more discrete spacers affixed to the absorbent article. As shown in FIG. 6, two spacers 50b may be positioned so that both spacers are disposed between the flap 30 and the topsheet 12 on opposite sides of the longitudinal axis 48. One of the illustrated spacers 50b is positioned in proximity to the first terminal end of the seam 42 while the second illustrated spacer 50b is positioned in proximity to the second terminal end of the seam 44. When the opening 40 extends substantially laterally and the spacers are positioned on opposite sides of the longitudinal axis 48, as illustrated in FIG. 6, the laterally central portion of the opening, which is laterally disposed between the two spacers 50b, will be biased away from the topsheet 12 and be clear of obstructions. Thus, the laterally central portion of the opening 40 will provide a clear passageway for receiving fecal materials into the pocket.

Spacers 50b are formed in manner similar to spacers 50a but have a rectangular rather than triangular shape. It is generally advantageous for the spacer to have a minimum width which is at least one half of the height of the spacer to provide stability to the spacer. Spacers 50b include a folded hinge 70 which is positioned opposite free edge 38.

Where two spacers are used on opposite sides of the longitudinal axis 48, the spacers may be advantageously spaced apart by approximately 2.54 to 10.16 cm (1 to 4 inches), with spacings of approximately 5.08 cm (2 inches) and between 7.62 to 10.16 cm (3 to 4 inches) being well adapted for use with disposable diapers. Where two such spacers are employed on opposite sides of the longitudinal axis 48, the spacers may take a variety of different shapes and configurations. For example, the spacers may have a thickness ranging from about 1 mm to about 4 cm, Widths (i.e., greatest lateral extension) thickness ranging from about 1 cm to about 4 cm, and lengths (i.e., greatest longitudinal extension) of from about 1 cm to about 10 cm.

In the embodiment illustrated in FIG. 6 the spacers 50b are positioned in parallel and symmetrically about the longitudinal axis 48. Alternative embodiments employing spacers on opposite sides of the longitudinal axis 48, however, may use spacers which are not necessarily positioned in parallel or positioned symmetrically about the longitudinal axis.

The use of an absorbent material to form all or a portion of the spacer can provide the pocket with an enhanced absorbent capacity for absorbing fecal fluids. The use of absorbent spacers thereby further enhances the ability of the pocket to retain fecal materials. Fibrous materials can provide void spaces in the spacer which may entrap small fecal particulates. An enhanced absorbent capacity and the ability to entrap fecal particulates is particularly advantageous for use with fecal materials having a high fluid content such as those often produced by small infants.

In addition to single and multiple layer fibrous webs of natural or synthetic fibers or combinations thereof, suitable materials for the spacers include single or multiple layers of a foam material. For example, a crosslinked polyethylene foam material which is commercially available from Sentinel Foams, a business having offices in Hyannis, Massachusetts under the trade designation EMR NAT may be used to form a spacer. An open celled polyester based foam material commercially available from Woodbridge Foam Fabricating, Inc., having offices in Chattanooga, Tenn., under the trade designation SM-25 BIOFREE ELASTICIZED FOAM may be used to form spacers. Such foam materials can be absorbent and may thereby provide the pocket with an enhanced capacity for retaining fluids as discussed above.

Both foam and fibrous materials which provide such an enhanced absorbent capacity will often behave as a sponge, with those portions of the spacer which are under reduced compressive forces having a greater absorbency than those portions of the spacer experiencing higher compressive forces.

Fibrous layers may be used in the manufacture of a spacer and can be formed of a meltblown or spunbonded web of polyolefin fibers, a fibrous bonded-carded web, or an airlaid web. Fibrous spacers may also advantageously employ bicomponent fibers such as fibers having a polyethylene sheath and a polyester core. The spacer fibers may also be treated to impart wettability and hydrophilicity to the fibers. Some of the fibrous nonwoven materials which may be used in the manufacture of a spacer include materials such as a hydro-entangled nonwoven material obtained from E.I. Dupont de Nemours under the trade designation SONTARA 8423. Alternative embodiments of the present invention may include a dynamic spacer in combination with an auxiliary fibrous material disposed between the flap and topsheet which does not include a biasing element. Such an auxiliary fibrous material would provide assistance in maintaining the separation of the flap 30 from the topsheet 12 and also provide an absorbent structure within the pocket formed by the flap 30 and topsheet 12. For example, such an auxiliary fibrous material could be located along the rear of the pocket near or adjacent rear seam 36a.

A variety of additional flexible materials may also be used to form at least a portion of the spacers described herein. Such materials may include rubbery-like films, ethylene vinyl acetate ("EVA"), polyethylene, urethane, polyester, polypropylene, metallocene, natural rubber, mylar, tygon and similar materials.

In some embodiments of the present invention, the bodyside major surface 32 of the flap 30 may include adhesive areas 76 as illustrated in FIG. 4. Adhesive areas 76 which are positioned on the bodyside surface 32 of the flap 30 are intended to secure the flap to the skin of the wearer. By adhering the flap to the skin of the wearer, the formation of a gap between the absorbent article and the skin of the wearer, through which bodily exudates might escape, is further inhibited and the pocket is maintained in an open position.

Adhesives which are capable of adequately securing a fabric to skin without causing damage to the skin upon disengagement are suitable for forming the adhesive areas 76. Additionally, the adhesive area 76 should not irritate the skin of any appreciable number of wearers.

Suitable adhesives may include hydrogels, silicones, acrylics, polyurethanes, polyesters, and polyamides. Other suitable adhesives include rubber-based adhesives such as those based on styrenebutadiene, polyisobutylene, polybutadiene and polyisoprene; water soluble adhesives such as those based on polyvinyl alcohol, polyvinyl acetate and methyl cellulose; and hot melt adhesives such as those based on block copolymers of styrene-butadiene-styrene, styrene-isoprene-styrene, steyrene-ethylenepropylene-styrene, styrene-ethylenebutylene-styrene, and tetrablock copolymers such as styrene-ethylenepropylene-styrene-ethylenepropylene. Additional suitable adhesives may also include other substances such as tackifying resins, oils and the like.

Advantageously, the adhesive areas 76 of the present invention may be formed using a polysiloxane material. As used herein, a "polysiloxane material" is intended to represent a polymeric material that includes alternate silicon and oxygen atoms with hydrogen or various organic groups attached to the silicon. A detailed description of polysiloxane adhesives is provided in the disclosure of U.S. Pat. No. 5,618,281, issued Apr. 8, 1997 to Betrabet et al., and the disclosure of this patent is incorporated herein by reference.

Starting materials useful in preparing the polysiloxane adhesive composition of the present invention, such as lower alkenyl-functional polysiloxane materials and hydrogen containing polysiloxane copolymer materials containing active hydrogen groups, are well known and may be commercially obtained from such vendors as the Dow Corning Corporation, Wacker Silicones Corporation, and General Electric Corporation.

Fumed silica may also be added to the polysiloxane composition to provide an adhesive area 76 which is adapted for securing a fabric to the skin of a wearer. For example, a two-part polysiloxane adhesive obtained from the Dow Corning Corporation under the trade designation Sylgard Q3-6636 silicone dielectric gel adhesive parts A and B may be mixed with fumed silica obtained from Aldrich Chemical Company to provide a suitable adhesive area 76. The adhesive was prepared by mixing 8 grams Dow Corning 6636A with 8 grams Dow Corning 6636B. Fumed silica having an approximate particle size of 0.007 microns was also added to the mixture in the amount of 0.48 grams or less. Polysiloxane adhesives often have an oily feel and the addition of fumed silica can reduce this attribute.

The adhesive areas 76 may be placed on the flaps in either a single contiguous area or in a plurality of discrete, spaced areas. Although the adhesive areas may be located at alternative locations on the flaps, the adhesive areas 76 are advantageously positioned on the laterally central portion of the flap which is adjacent the free edge 38 as shown in FIG. 4. The use of such adhesives on a rear flap is disclosed in U.S. patent application Ser. No. 09/215,493 entitled Absorbent Article with Adhesive Flap, filed Dec. 18, 1998, the disclosure of which is hereby incorporated by reference.

The material used to form the flap 30 may be either liquid permeable or liquid impermeable. It is generally preferred that the flap 30 be formed from a material which is substantially impermeable to liquids. Flap 30 may be formed from a single unitary layer of material or by a laminate material comprising several individual layers. For example, the flap may be formed from a thin plastic film or other flexible liquid-impermeable material such as a polyethylene film having a thickness of from about 0.013 millimeter (0.5 mil) to about 0.051 millimeter (2.0 mils).

If it is desired to present a more clothlike feeling, the flap 30 may comprise a polyethylene film having a nonwoven web laminated to the bodyside surface 32, such as a spunbond web of polyolefin fibers. For example, a polyethylene film having a thickness of about 0.015 millimeter (0.6 mil) may be thermally laminated to a spunbond web of polyolefin fibers, with the fibers having a thickness of about 1.5 to 2.5 denier per filament and the nonwoven web produced thereby having a basis weight of about 24 grams per square meter (0.7 ounce per square yard). Methods of forming such clothlike layers are known to those skilled in the art.

Further, the flap 30 may be formed of a woven or nonwoven fibrous web layer which has been totally or partially constructed or treated to impart a desired level of liquid impermeability. Still further, the flap 30 may optionally be composed of a micro-porous "breathable" material which permits vapors to pass through the flap 30 while still preventing liquid exudates from passing through the flap 30. The backsheet 14 may be formed using the same materials as those used for the flap 30.

Flap 30 may also include elastomeric materials. For example, the flap 30 may be formed by, or include, a stretch-bonded-laminate (SBL) material, a neck-bonded-laminate (NBL) material, an elastomeric film, an elastomeric foam, or similar elastomeric material.

A non-elastomeric flap may also be modified to render portions of the flap elastically contractable to contour the flap to the wearer's body. As illustrated in FIG. 1, different portions of the flap may include elastic strands 78 which are laterally elongated and adhesively attached to the flap. Suitable elastic strands are known to those skilled in the art. For example, a suitable elastic strand may be composed of a 470 decitex Lycra elastomer or a 620 decitex Lycra elastomer, which are obtainable from E.I. DuPont de Nemours Co., or similar elastomers. Alternatively, a piece of elastomeric material, e.g., an SBL, NBL or elastomeric film or foam, may be adhesively attached to selected portions of the flap in an elongated condition to provide the desired elasticity. The flap 30 may also employ alternative configurations of elastic areas such as longitudinally oriented elastic areas.

The flap 30 may also include an absorbent material 80 located on the bodyside surface 32 of the flap as illustrated in FIG. 4. Absorbent material 80 provides a means for absorbing and containing small quantities of waste materials which may be present at the body facing surface of the flap. Adhesive areas 76 are configured to prevent escape of bodily exudates, however, it may still be possible for minor quantities of fecal fluids and particulates to occasionally migrate between the flap and the wearer's skin. Thus, although the absorbent material 80 has only a small absorbent capacity in comparison to the absorbent structure 16, the functioning of the flap should prevent any significant quantities of waste fluids from reaching the area between the flap and the wearer's skin.

Fecal fluids may produce noticable staining, even when present in only minor quantities, if absorbed by the clothing of the wearer or caregiver. Furthermore, it is undesirable for skin health and cleanliness reasons for such fluids to contact the skin of the wearer or caregiver. Thus, the provision of an absorbent material 80 with only a small total absorbent capacity provides a valuable function. By utilizing a fibrous material to form the absorbent material 80, the absorbent material will include void spaces between the fibers which may retain small quantities of fecal particulate matter in addition to fluids.

The absorbent material 80 may cover all or part of the bodyside surface 32 of the flap 30. As illustrated in FIG. 4, the absorbent material 80 may be advantageously positioned laterally central and longitudinally forward on the flap. The front edge of absorbent material 80 may be positioned near the free edge 38 of the flap and is advantageously spaced at least about 0.5 cm rearwardly of the free edge 38 of the flap. The rear edge of the absorbent material 80 is advantageously spaced forward of rear edge 28 of the absorbent article. The rear edge 28 of the article may come into contact with a caregiver or the clothing or bedding materials of the wearer and it is desirable for this edge to not include an exposed layer of saturated absorbent material.

The basis weight of the absorbent material 80 may be varied and suitable basis weights include at least about 30 grams per square meter, at least about 50 grams per square meter, and at least about 75 grams per square meter. The absorbent material 80 may be joined to the flap in a variety of manners such as by heat sealing, sonic bonding, adhesives and other attachment methods known in the art.

A number of different materials may be used to form the absorbent material 80. For example, the absorbent material 80 can include a nonwoven material such as a spunbond, meltblown, spun laced or carded web of natural fibers, synthetic fibers, polymeric fibers, similar fibrous materials, or combinations thereof. Alternatively, the absorbent material 80 may include a foam material or an uncreped through air dried material comprising cellulosic fibers.

Desirably, the absorbent material 80 includes hydrophilic fibers such as cellulose or rayon fibers. Nonwoven materials formed from hydrophobic materials, however, may be treated with a surfactant to render them generally hydrophilic and such treated materials may also be used to form an effective absorbent material 80.

The fibers may also be oriented in one direction such that the absorbent material 80 will primarily wick fluid in that direction. For example, by providing an absorbent material having a fiber orientation direction which is in a substantially lateral direction, indicated by lateral line 49 in FIG. 4, the absorbent material 80 will tend to wick absorbed fluids in a lateral, rather than longitudinal, direction. Thus, the absorbed liquids will not have a tendency to migrate towards the rear edge 28 where an exposed edge of a saturated or wetted layer of material might come into contact with the clothing or bedding of the wearer or the skin or clothing of a caregiver.

In a specific embodiment, the absorbent material 80 may be formed from a nonwoven material such as a bonded carded web which includes natural fibers. One such material is a bonded carded web commercially available from E. I. DuPont de Nemours Co. a business having offices located in Delaware under the trade designation SONTARA 8423. Such material includes about 70 weight percent rayon fibers and about 30 weight percent polyester fibers and has a basis weight of about 78 grams per square meter. The use of such a material on a diaper containment flap is disclosed in U.S. application Ser. No. 08/984,347 of Barbara O. Sauer entitled "Absorbent Article Having Improved Containment Flaps" filed Dec. 3, 1997 and is incorporated herein by reference.

The topsheet 12 of the illustrated diaper 10 is a conventional liner and suitably presents a body facing surface which is compliant, soft feeling, and nonirritating to the wearers skin. The topsheet 12 may be advantageously employed to help isolate the wearer's skin from liquids held in the absorbent structure 16. For example, the topsheet may be less hydrophilic than the absorbent structure 16 to present a relatively dry surface to the wearer while remaining sufficiently porous to be liquid permeable, permitting liquid to readily penetrate through its thickness.

Suitable topsheet materials are well known in the art and include a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. One nonwoven fabric well-suited for use as topsheet 12 is a spunbond, polypropylene fabric composed of about 2.8–3.2 denier fibers formed into a web having a basis weight of about 22 grams per square meter and a density of about 0.06 gram per cubic centimeter and which has been surface treated with a surfactant.

The backsheet 14 of the illustrated diaper 10 typically provides the outer cover of the article and may be composed of either a liquid permeable or liquid impermeable material. It is often preferred, however, to form the backsheet 14 from a material which is substantially impermeable to liquids. A woven or nonwoven fibrous web layer which has been totally or partially constructed or treated to impart the desired level of liquid impermeability to the entire backsheet 14 or selected regions thereof that are adjacent or proximate the absorbent structure 16 may be advantageously employed as the backsheet 14. The backsheet 14 may optionally be composed of a micro-porous "breathable" material which permits vapors to escape from the absorbent structure 16 while still preventing liquid exudates from passing through the backsheet 14.

For example, a typical backsheet can be manufactured from a thin plastic film or other flexible liquid-impermeable material such as a polyethylene film having a thickness of from about 0.012 millimeter (0.5 mil) to about 0.051 millimeter (2.0 mils). If it is desired to present the backsheet with a more clothlike feeling, the backsheet 14 may include a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). The backsheet 14 can also be embossed or otherwise provided with a matte finish to impart a desired appearance or feel. Methods of forming such clothlike backsheets are known to those skilled in the art.

The topsheet 12 and backsheet 14 may be attached together so as to form an enclosure in which the absorbent structure 16 is located. The topsheet 12 and backsheet 14 may be so attached by either directly joining the topsheet 12 and backsheet 14 together or by attaching the topsheet 12 and backsheet 14 together via one or more intermediate components of the absorbent article. The side edges and longitudinal end edges of the disposable diaper 10 may be suitably formed by portions of the topsheet 12 and backsheet 14 which extend beyond the sides and longitudinal ends of the absorbent structure 16. The different components of the disposable diaper 10 may be bonded together by any means known to those skilled in the art such as adhesive bonding, ultrasonic bonding, thermal bonding and the like.

Absorbent materials suited for use as absorbent structure 16 are well known in the art. The absorbent structure 16 may comprise a matrix of hydrophilic fibers, such as a web of cellulosic fluff, mixed with particles of a high-absorbency material commonly known as superabsorbent material. In a particular embodiment, the absorbent structure 16 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent structure 16 may comprise a laminate of fibrous webs and superabsorbent material or other suitable means of maintaining a superabsorbent material in a localized area.

Suitable high-absorbency materials are well known in the art and may include natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

The absorbent structure 16 may have any of a number of shapes. For example, the absorbent structure may be rectangular, I-shaped, or T-shaped. It is generally preferred that the absorbent structure 16 be narrower in the intermediate section 22 than in the front 18 or rear 20 waist sections.

The absorbent structure may also include a surge layer to rapidly distribute liquids throughout the absorbent structure 16 and prevent the pooling of liquids on the topsheet 12. Such surge layers are well known in the art and are often disposed immediately below the bodyside liner.

As shown in FIGS. 1 and 2, diaper 10 may include two fastener tabs 82. The fastener tabs 82 have hook components which engage a loop component positioned on the front portion of backsheet 14 to secure the diaper 10 about the waist of the wearer in a manner which is well known in the art. Fastening components such as adhesive tapes, buttons, pins, snaps, mushroom and loop fasteners, and similar devices may alternatively be used to secure the diaper 10 about the waist of the wearer.

The diaper 10 may also include a pair of elasticized, longitudinally-extending leg cuffs 84 as illustrated in FIGS. 1–3. The leg cuffs 84 are generally adapted to fit about the legs of the wearer in use and serve as a mechanical barrier to the lateral flow of body exudates. If desired, the diaper 10 may also include a front and rear waist elastic to secure the diaper about the front and back waist of the wearer when in use. A front waist elastic member 86 is illustrated in FIG. 1. The leg cuffs 84 and waist elastics may be elasticized by elastic members as are well known to those skilled in the art. The diaper 10 may also include a pair of elasticized, longitudinally-extending containment flaps 88 which can be configured to maintain an upright, perpendicular arrangement in at least the intermediate section 22 of the diaper 10 to serve as an additional barrier to the lateral flow of body exudates.

While this invention has been described in detail, it will be readily apparent to a person of ordinary skill in the art that various changes and modifications can be made without departing from the spirit and general principles of the invention. All of such changes and modifications are contemplated as being within the scope of the present invention as defined by the subjoined claims. Furthermore, this application is intended to cover such departures from the present disclosure as come within known or customary practice in the art.

We claim:

1. An absorbent article having a bodyside surface positionable adjacent a wearer when the article is in use, the bodyside surface having a laterally central, longitudinal axis, said article comprising:

a backsheet;

a liquid permeable topsheet attached to said backsheet;

an absorbent structure disposed between said topsheet and said backsheet;

a flap laterally disposed in a rear waist portion of said article, said flap fixedly secured to said article along a seam, said seam extending between first and second terminal ends, said flap having a free edge extending between said first and second terminal ends, said seam and said free edge defining a pocket between said flap and said topsheet, said pocket having an opening extending between said first and second terminal ends; and a spacer assembly affixed to said article and operatively engaging an inside surface of the flap, said spacer assembly having a first element in contact with said flap, a second element disposed between said first element and said backsheet, and a biasing element forcibly separating said first and second elements wherein the biasing element and the first and second elements are cooperatively operable together independent of said flap and whereby said free edge is biased away from said topsheet.

2. The absorbent article of claim 1 wherein said spacer assembly further comprises a hinge pivotally connecting said first and second elements.

3. The absorbent article of claim 1 further comprising a second spacer assembly affixed to said article, said second spacer assembly having a third element in contact with said flap, a fourth element disposed between said third element and said backsheet, and a second biasing element forcibly separating said third and fourth elements;

said spacer assemblies respectively positioned in proximity to said first terminal end and said second terminal end; and said opening extending substantially laterally whereby said spacer assemblies are disposed on opposite sides of the longitudinal axis and a laterally central portion of said free edge is laterally disposed between said spacer assemblies and biased away from said topsheet.

4. The absorbent article of claim 1 wherein one of said elements extends through said opening.

5. The absorbent article of claim 1 wherein said spacer assembly comprises a folded material.

6. The absorbent article of claim 1 wherein said biasing element is formed by a resilient hinge comprising a folded material.

7. The absorbent article of claim 1 wherein said spacer assembly is disposed near said longitudinal axis.

8. The absorbent article of claim 7 wherein said spacer assembly is a folded foam material.

9. An absorbent article having a bodyside surface positionable adjacent the crotch and rear waist region of a wearer when the article is in use, the bodyside surface having a laterally central longitudinal axis, said article comprising:

a backsheet;

a liquid permeable topsheet attached to said backsheet;

an absorbent structure disposed between said topsheet and said backsheet;

a laterally extending flap disposed in a rear waist portion of said article, said flap attached to said article along a seam, said seam extending between first and second terminal ends, said flap having a free edge extending between said first and second terminal ends, said seam and said free edge defining a pocket between said flap and said topsheet, said pocket having an opening extending between said first and second terminal ends; and a spacer affixed to said article and operatively engaging an inside surface of the flap, said spacer having a first element contacting said flap, a second element contacting said topsheet, and a biasing element forcibly separating said first and second elements wherein the biasing element and the first and second elements are cooperatively operable together independent of said flap and whereby said free edge is biased away from said topsheet.

10. The absorbent article of claim 9 wherein said spacer further comprises a hinge pivotally connecting said first and second elements.

11. The absorbent article of claim 9 further comprising a second spacer affixed to said article, said second spacer having a third element contacting said flap, a fourth element contacting said topsheet, and a second biasing element forcibly separating said third and fourth elements;

said spacers respectively positioned in proximity to said first terminal end and said second terminal end; and said opening extending substantially laterally whereby said spacers are disposed on opposite sides of the longitudinal axis and a laterally central portion of said free edge is laterally disposed between said spacers and biased away from said topsheet.

12. The absorbent article of claim 9 wherein one of said elements extends through said opening.

13. The absorbent article of claim 9 wherein said spacer comprises a folded material.

14. The absorbent article of claim 10 wherein said hinge and said biasing element are both formed by a fold.

15. The absorbent article of claim 9 wherein said spacer is disposed near said longitudinal axis.

16. The absorbent article of claim 15 wherein said spacer is a folded foam material.

17. The absorbent article of claim 9 wherein said flap is liquid impermeable.

* * * * *